(12) United States Patent
Donovan

(10) Patent No.: US 7,138,127 B1
(45) Date of Patent: Nov. 21, 2006

(54) CLOSTRIDIAL TOXIN DERIVATIVES AND METHODS FOR TREATING PAIN

(75) Inventor: **

OTHER PUBLICATIONS

XP001011386, Garzon, J et al., "Effect of intrathecal injection of pertusis toxin on substance P norepinephrine and serotonin contents in various neural structures of arthritic rats"; Life Sciences; 47(21):1915-1924 (1990).

Ueda, "In Vivo Molecular Signal Transduction . . . " Jpn J Pharmacol. vol. 79, 1999, pp. 263-268, only abstract.

Nichols et al, "Transmission of Chronic Nociception . . . " Science, vol. 286, Nov. 1999, pp. 1558-1561.

Lopes & Couture, "Localization of Bradykinin-Like . . . " Neuroscience, vol. 78, 1997, pp. 481-497, only abstract.

Vigna et al, "Characterization of Antibodies . . . " J Nerosci, vol. 14, 1994, pp. 834-845, only abstract.

Principles of Neural Science Third Edition, Edited by Kandel et al, one page (1991).

Babenko etal, "Experimental Human Muscle Pain . . . " Pain, vol. 82, 1999, pp. 1-8.

Garrison & Rall, "Autacoids; Drug Therapy of Inflammation".

Henry, "Substance P and Inflammatory . . . " Disease Therapy, 1993.

Tsuda et al "In Vivo Pathway . . . " Br J Pharmacol, vol. 127, 1999, pp. 449-456.

Welch et al, "Sensitivity of Emryonic Rat . . . " Toxicon, vol. 38, 2000, pp. 245-258.

Mathias et al, "Topical Casaicin for Chronic Neck Pain.." Abstract,American Journal of Physical Medicine &Rehabilitation,vol. 74,1995,pp. 39-44.

Furst, "Transmitters Involved in Antinociception in the Spinal Cord" Abstract, Brain Research Bulletin, vol. 48, 1999, pp. 129-141.

Poulain et al, Inhibition of Transmitter Release by *botulinum* Neurotoxin A Eur.J.Biochem, vol. 185, 1989, pp. 197-203.

van Hagen et al, "Neuropeptides and Their Receptors" Ann Med, vol. 31 Suppl2, pp. 15-22, (Oct. 1999).

* cited by examiner

CLOSTRIDIAL TOXIN DERIVATIVES AND METHODS FOR TREATING PAIN

BACKGROUND

The present invention relates to compositions and methods for treating pain. In particular, the present invention relates to Clostridial toxin derivatives, methods for making the Clostridial toxin derivatives and methods for treating pain using the Clostridial toxin derivatives.

Many, if not most aliments of the body cause pain. The causes of pain can include inflammation, muscle spasm and the onset of a neuropathic event or syndrome. Inflammatory pain can occur when tissue is damaged, as can result from surgery or due to an adverse physical, chemical or thermal event or to infection by a biologic agent. Spasticity or muscle spasm can be a serious complication of trauma to the spinal cord or other disorders that create damage within the spinal cord. Muscle spasm is often accompanied by pain. The pain experienced during a muscle spasm can result from the direct effect of the muscle spasm stimulating mechanosensitive pain receptors or from the indirect effect of the spasm compressing blood vessels and causing ischemia. Since the spasm increases the rate of metabolism in the affected muscle tissue, the relative ischemia becomes greater creating thereby conditions for the release of pain inducing substances. Neuropathic pain is a persistent or chronic pain syndrome that can result from damage to the nervous system, the peripheral nerves, the dorsal root ganglion or dorsal root, or to the central nervous system.

Neuropathic pain syndromes include allodynia, various neuralgias such as post herpetic neuralgia and trigeminal neuralgia, phantom pain, and complex regional pain syndromes, such as reflex sympathetic dystrophy and causalgia. Causalgia is characterized by spontaneous burning pain combined with hyperalgesia and allodynia.

Pain can be experienced when the free nerve endings which constitute the pain receptors in the skin as well as in certain internal tissues are subjected to mechanical, thermal or chemical stimuli. The pain receptors transmit signals along afferent neurons into the central nervous system and thence to the brain.

The transduction of sensory signals, such as pain signals, from the periphery to sensation itself is achieved by a multi-neuronal pathway and the information processing centers of the brain. The first nerve cells of the pathway involved in the transmission of sensory stimuli are called primary sensory afferents. The cell bodies for the primary sensory afferents from the head and some of the internal organs reside in various ganglia associated with the cranial nerves, particularly the trigeminal nuclei and the nucleus of the solitary tract. The cell bodies for the primary sensory afferents for the remainder of the body lie in the dorsal root ganglia of the spinal column. The primary sensory afferents and their processes have been classified histologically; the cell bodies fall into two classes: A-types are large (60–120 micrometer in diameter) while B-types are smaller (14–30 micrometer) and more numerous. Similarly the processes fall into two categories: C-fibers lack the myelin sheath that A-fibers possess. A-fibers can be further sub-divided into A beta-fibers, that are large diameters with well developed myelin, and A delta-fibers, that are thinner with less well developed myelin. It is generally believed that A beta-fibers arise from A-type cell bodies and that A delta- and C-fibers arise from B-type cell bodies.

After the activation of the primary sensory afferents the next step in the transduction of sensory signals is the activation of the projection neurons, which carry the signal, via the spinothalamic tract, to higher parts of the central nervous system such as the thalamic nuclei. The cell bodies of these neurons (other than those related to the cranial nerves) are located in the dorsal horn of the spinal cord. This is also where the synapses between the primary afferents and the projection neurons are located. The dorsal horn is organized into a series of laminae that are stacked, with lamina I being most dorsal followed by lamina II, etc. The different classes of primary afferents make synapses in different laminae. For cutaneous primary afferents, C-fibers make synapses in laminae I and II, A delta-fibers in laminae I, II, and V, and A beta-fibers in laminae III, IV, and V. Deeper laminae (V–VII, X) are thought to be involved in the sensory pathways arriving from deeper tissues such as muscles and the viscera.

The predominant neurotransmitters at the synapses between primary afferents and projection neurons are substance P, glutamate, calcitonin-gene related peptide (CGRP) and neuropeptide Y. The efficiency of transmission of these synapses can be altered via descending pathways and by local interneurons in the spinal cord. These modulatory neurons release a number of mediators that are either inhibitory (e.g. opioid peptides, glycine) or excitatory (e.g. nitric oxide, cholecystokinin), to provide a mechanism for enhancing or reducing awareness of sensations.

Effective pain alleviating drugs are needed. It is known that intraspinal administration of opioids, such as morphine and fentanyl can alleviate pain. See e.g. Gianno, J., et al., *Intrathecal Drug Therapy for Spasticity and Pain*, Springer-Verlag (1996) (which publication is incorporated herein by reference in its entirety). Unfortunately, current drugs used in intraspinal, or intrathecal, injections typically have only short lived antinociceptive effects. As a result, these drugs have to be frequently administered, such as by the aid of a pump for continuous infusion. For example, one frequently used pump is the SynchroMed® Infusion System, a programmable, implanted pump available from Medtronic, Inc., of Minneapolis, Minn. However, complications can arise due to the required surgical implantation procedure for the use of the pump and the known intrathecally administered drugs for pain, such as opioids, have the disadvantages of dependency and potential respiratory depression.

Longer acting analgesics are also known, for example, blocks by phenol injection. However, such treatments raise a considerable risk of irreversible functional impairment.

Intrathecal administration of *botulinum* toxin type B to mice to treat thermal hyperalgesia is known. *Br. J. Pharmacol* 1999;127(2):449–456. Additionally, it has been reported (*Science*, 1999; 286:1558–1561) ("Nichols et al.") that intrathecal injection of a cytotoxic saporin-substance P (saporin can be abbreviated as "SAP" and substance P can be abbreviated as "SP") conjugate (which can be abbreviated as SAP-SP) results in a reduction of thermal hyperalgesia and mechanical allodynia.

As discussed in Nichols et al, supra, spinothalamic and spinoparabrachial neurons are involved in the ascending conduction of acute noxious stimuli. Apparently, these neurons are projection neurons and can be targeted by substance P. When a conjugate of the ribosome-inactivating protein saporin and SP was intrathecally infused into the spinal cord, the SAP-SP conjugate is stated to have specifically concentrated in the projection neurons, apparently because these neurons express cell surface receptors for substance P (a substance P receptor can be abbreviated as "SPR"). Unfortunately, the SAP-SP targeted neurons are killed by the SAP.

Although SAP-SP is specific for projection neurons because projection neurons appear to express the SPR, an intrathecal injection of SAP-SP may cause necrosis of other neurons through non-specific or low affinity SAP-SP neuronal interactions. For example, SAP-SP may interact with and cause motor neurons cell death. Since motor neurons and most other neurons in the spinal cord do not regenerate, it is contraindicated to use SAP-SP in humans, unless destruction of the neurons with the resulting in permanent disablement, and for example, paralysis, is a desired end result. Clearly it would be desirable to be able to treat pain, including chronic pain, without causing necrosis and irreversible loss of the neurons treated.

Botulinum Toxin

The anaerobic, gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

*Botulinum* toxin type A is the most lethal natural biological agent known to man. About 50 picograms of *botulinum* toxin (purified neurotoxin complex) type A is a $LD_{50}$ in mice. One unit (U) of *botulinum* toxin is defined as the $LD_{50}$ upon intraperitoneal injection into female Swiss Webster mice weighing 18–20 grams each. Seven immunologically distinct *botulinum* neurotoxins have been characterized, these being respectively *botulinum* neurotoxin serotypes A, B, $C_1$, D, E, F and G each of which is distinguished by neutralization with type-specific antibodies. The different serotypes of *botulinum* toxin vary in the animal species that they affect and in the severity and duration of the paralysis they evoke. For example, it has been determined that *botulinum* toxin type A is 500 times more potent, as measured by the rate of paralysis produced in the rat, than is *botulinum* toxin type B. Additionally, *botulinum* toxin type B has been determined to be non-toxic in primates at a dose of 480 U/kg which is about 12 times the primate $LD_{50}$ for *botulinum* toxin type A. *Botulinum* toxin apparently binds with high affinity to cholinergic motor neurons, is translocated into the neuron and blocks the release of acetylcholine.

*Botulinum* toxins have been used in clinical settings for the treatment of neuromuscular disorders characterized by hyperactive skeletal muscles. *Botulinum* toxin type A has been approved by the U.S. Food and Drug Administration for the treatment of blepharospasm, strabismus and hemifacial spasm. Non-type A *botulinum* toxin serotypes apparently have a lower potency and/or a shorter duration of activity as compared to *botulinum* toxin type A. Clinical effects of peripheral intramuscular *botulinum* toxin type A are usually seen within one week of injection. The typical duration of symptomatic relief from a single intramuscular injection of *botulinum* toxin type A averages about three months.

Although all the *botulinum* toxins serotypes apparently inhibit release of the neurotransmitter acetylcholine at the neuromuscular junction, they do so by affecting different neurosecretory proteins and/or cleaving these proteins at different sites. For example, *botulinum* types A and E both cleave the 25 kiloDalton (kD) synaptosomal associated protein (SNAP-25), but they target different amino acid sequences within this protein. *Botulinum* toxin types B, D, F and G act on vesicle-associated protein (VAMP, also called synaptobrevin), with each serotype cleaving the protein at a different site. Finally, *botulinum* toxin type $C_1$ has been shown to cleave both syntaxin and SNAP-25. These differences in mechanism of action may affect the relative potency and/or duration of action of the various *botulinum* toxin serotypes.

Regardless of serotype, the molecular mechanism of toxin intoxication appears to be similar and to involve at least three steps or stages. In the first step of the process, the toxin binds to the presynaptic membrane of the target neuron through a specific interaction between the H chain and a cell surface receptor; the receptor is thought to be different for each type of *botulinum* toxin and for tetanus toxin. The carboxyl end segment of the H chain, $H_c$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino end segment of the H chain, $H_N$, which triggers a conformational change of the toxin in response to a pH of about 5.5 or lower. Endosomes are known to possess a proton pump which decreases intra endosomal pH. The conformational shift exposes hydrophobic residues in the toxin, which permits the toxin to embed itself in the endosomal membrane. The toxin then translocates through the endosomal membrane into the cytosol.

The last step of the mechanism of *botulinum* toxin activity appears to involve reduction of the disulfide bond joining the H and L chain. The entire toxic activity of *botulinum* and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, *botulinum* toxin/B/D, /F, and /G cause degradation of synaptobrevin (also called vesicle-associated membrane protein (VAMP)), a synaptosomal membrane protein. Most of the VAMP present at the cytosolic surface of the synaptic vesicle is removed as a result of any one of these cleavage events. Each toxin specifically cleaves a different bond.

The molecular weight of the *botulinum* toxin protein molecule, for all seven of the known *botulinum* toxin serotypes, is about 150 kD. Interestingly, the *botulinum* toxins are released by Clostridial *bacterium* as complexes comprising the 150 kD *botulinum* toxin protein molecule along with associated non-toxin proteins. Thus, the *botulinum* toxin type A complex can be produced by Clostridial *bacterium* as 90° kD, 500 kD and 300 kD forms. *Botulinum* toxin types B and $C_1$ is apparently produced as only a 500 kD complex. *Botulinum* toxin type D is produced as both 300 kD and 500 kD complexes. Finally, *botulinum* toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the *botulinum* toxin molecule comprise the relevant neurotoxin complex) may act to provide stability against denaturation to the *botulinum* toxin molecule and protection against digestive acids when toxin is ingested.

Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine, CGRP and glutamate.

*Botulinum* toxin type A can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the *botulinum* toxin type B serotype only cleave a portion of the toxin produced. The exact proportion of nicked to unnicked molecules depends on the length of incubation and the temperature of the culture. Therefore, a certain percentage of any preparation of, for example, the *botulinum* toxin type B toxin is likely to be inactive, possibly accounting for the known significantly lower potency of *botulinum* toxin type B as compared to *botulinum* toxin type A. The presence of inactive *botulinum* toxin molecules in a clinical preparation will contribute to the overall protein load of the preparation, which has been linked to increased antigenicity, without contributing to its clinical efficacy. Additionally, it is known that *botulinum* toxin type B has, upon intramuscular injection, a shorter duration of activity and is also less potent than *botulinum* toxin type A at the same dose level.

It has been reported that *botulinum* toxin type A has been used in clinical settings as follows:

(1) about 75–125 units of BOTOX®[1] per intramuscular injection (multiple muscles) to treat cervical dystonia;

[1]Available from Allergan, Inc., of Irvine, Calif. under the tradename BOTOX®.

(2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U (b) flexor digitorum sublimus: 7.5 U to 30 U (c) flexor carpi ulnaris: 10 U to 40 U (d) flexor carpi radialis: 15 U to 60 U (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

The success of *botulinum* toxin type A to treat a variety of clinical conditions has led to interest in other *botulinum* toxin serotypes. A study of two commercially available *botulinum* type A preparations (BOTOX® and Dysport®) and preparations of *botulinum* toxins type B and F (both obtained from Wako Chemicals, Japan) has been carried out to determine local muscle weakening efficacy, safety and antigenic potential. *Botulinum* toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or *botulinum* toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for *botulinum* toxin type B or 0.15 ng/kg for BOTOX®). Peak muscle weakness and duration were dose related for all serotypes. DAS $ED_{50}$ values (units/kg) were as follows: BOTOX®: 6.7, Dysport®: 24.7, *botulinum* toxin type B: 27.0 to 244.0, *botulinum* toxin type F: 4.3. BOTOX® had a longer duration of action than *botulinum* toxin type B or *botulinum* toxin type F. Therapeutic index values were as follows: BOTOX®: 10.5, Dysport®: 6.3, *botulinum* toxin type B: 3.2. Water consumption was greater in mice injected with *botulinum* toxin type B than with BOTOX®, although *botulinum* toxin type B was less effective at weakening muscles. After four months of injections 2 of 4 (where treated with 1.5 ng/kg) and 4 of 4 (where treated with 6.5 ng/kg) rabbits developed antibodies against *botulinum* toxin type B. In a separate study, 0 of 9 BOTOX® treated rabbits demonstrated antibodies against *botulinum* toxin type A. DAS results indicate relative peak potencies of *botulinum* toxin type A being equal to *botulinum* toxin type F, and *botulinum* toxin type F being greater than *botulinum* toxin type B. With regard to duration of effect, *botulinum* toxin type A was greater than *botulinum* toxin type B, and *botulinum* toxin type B duration of effect was greater than *botulinum* toxin type F. As shown by the therapeutic index values, the two commercial preparations of *botulinum* toxin type A (BOTOX® and Dysport®) are different. The increased water consumption behavior observed following hind limb injection of *botulinum* toxin type B indicates that clinically significant amounts of this serotype entered the murine systemic circulation. The results also indicate that in order to achieve efficacy comparable to *botulinum* toxin type A, it is necessary to increase doses of the other serotypes examined. Increased dosage can comprise safety. Furthermore, in rabbits, type B was more antigenic than was BOTOX®, possibly because of the higher protein load injected to achieve an effective dose of *botulinum* toxin type B.

The tetanus neurotoxin acts mainly in the central nervous system, while *botulinum* neurotoxin acts at the neuromuscular junction; both act by inhibiting acetylcholine release from the axon of the affected neuron into the synapse, resulting in paralysis. The effect of intoxication on the affected neuron is long-lasting and until recently has been thought to be irreversible. The tetanus neurotoxin is known to exist in one immunologically distinct type.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic and most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of the heart by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and insulin, respectively, from large dense-core vesicles. The PC12 cell line is a clone of rat pheochromocytoma cells extensively used as a tissue culture model for studies of sympathoadrenal development. *Botulinum* toxin inhibits the release of both types of compounds from both types of cells in vitro, permeabilized (as by electroporation) or by direct injection of the toxin into the denervated cell. *Botulinum* toxin is also known to block release of the neurotransmitter glutamate from cortical synaptosomes cell cultures.

U.S. Pat. No. 5,989,545 ("Foster et al.") (incorporated herein by reference in its entirety) discusses conjugating clostridial neurotoxins to targeting moieties in order to direct the inhibitory effect of clostridial neurotoxins toward primary sensory afferent neurons. Thus, the mechanism by which the agents disclosed by Foster et al alleviate pain is as follows: the targeting moieties of the agents, for example the growth factors, bind to receptor sites on the sensory afferent nerve terminals, for example the growth factor receptors, in the spinal cord; then, the clostridial neurotoxins, along with the conjugated targeting moieties, translocate into the nerve terminal and inhibit the release of one or more transmitters involved in the signaling of pain, and thereby alleviate pain.

Unlike SAP-SP, the clostridial-targeting moiety conjugates disclosed by Foster et al do not appear to be cytotoxic. Despite their superiority to the SAP-SP in that they are non-cytotoxic, they are still inadequate as pain alleviating agents because they lack the specificity for treating pain. More particularly, the Foster et al's targeting moieties intended for primary sensory afferent neurons are non-specific.

Thus, the agents disclosed by Foster et al are non-specific because their targeting moieties are not known to bind to receptors specifically and to primarily localize to primary sensory afferent nerve terminals. Therefore, the targeting moieties disclosed by Foster et al. may readily bind to receptors on neuronal terminals, or neurons, that are not primary sensory afferent synaptic terminals. For example, the targeting moiety comprising nerve growth factor disclosed by Foster et al may readily bind to receptors on nerve terminals and neurons other than the receptors on the primary sensory afferent nerve terminals, because nerve growth factor receptors are found on most neurons. As such, the clostridial neurotoxin conjugate disclosed by Foster et al may bind to one of these other neurons, for example the neurons involved in the sympathetic pathway, translocate into their cytosol, inhibit the release of their neurotransmitters, and thereby inhibiting their functions. Such random, non-specific inhibition may cause undesirable side effects during the treatment of pain.

Similarly, bradykinin, another targeting moieties disclosed by Foster et al, have been shown to have high density concentration in the motor neurons of the ventral horn in the spinal cord. (See Lopes et al, *Neuroscience* 78(2):481–497, the content of which is incorporated in its entirety herein by reference.) Agents disclosed by Foster et al which bear bradykinins as targeting moieties will significantly interact and interfere with motor functions when the agents are injected intraspinally to treat pain.

Also, the opioid receptor binding targeting moieties disclosed by Foster et al, for example, methionine-enkephalin, are non-specific with respect to directing the clostridial neurotoxin to the primary sensory afferent nerve terminal. Kandel et al, *Principles of Neural Science*, third edition, page 395, (1991), indicated that opioid receptors are widely distributed throughout the central nervous system, suggesting that opioid receptors, when activated, modulate physiological functions other than pain. Therefore, the clostridial neurotoxin-targeting moiety, as disclosed by Foster et al, may bind to and interfere with cells having opioid receptors but are not involved in the pain pathway. When this non-specific binding and interference occur, undesirous side effects may result.

What is needed therefore is an specific (high affinity) therapeutically effective, long duration non-cytotoxic agent and method for treating pain.

SUMMARY

The present invention meets this need by providing specific (high affinity) therapeutically effective, long duration non-cytotoxic agents and methods for treating pain. I have discovered agents effective in alleviating pain, methods of making such agents and methods of using such agents to alleviate pain. The present invention provides non-cytotoxic agents for treating pain which preferably have one or more of the characteristics of long duration of activity and specificity for the treatment of pain with limited or substantially insignificant side effects at therapeutic dose levels. Furthermore, the methods of producing these agents are relatively straight forward and effective to provide the desired results.

In one broad aspect of the invention, agents are provided comprising a clostridial neurotoxin or component thereof coupled to a targeting moiety selected from the group consisting of transmission compounds released from neurons in transmitting pain signals and compounds substantially similar to the transmission compounds.

In one preferred embodiment, the clostridial neurotoxin component is covalently coupled to the targeting moiety. The clostridial neurotoxin component may, for example, be derived (i.e. made or secreted by) from Clostridial *beratti*, Clostridial *butyricum*, or Clostridial *botulinum*. More preferably, the *clostridium* neurotoxin component is derived from (that is, is made or secreted by) a Clostridial *botulinum* bacterium. Although it is preferable that *botulinum* neurotoxin type A is used, other types, for example, types B, C, D, E, F, G and mixtures thereof, may be employed.

The *clostridium* neurotoxin component preferably includes at least one of a heavy chain and a light chain of a clostridial neurotoxin. The clostridial neurotoxin component may comprise only fragments of the entire neurotoxin. For example, in one embodiment, the $H_C$ of the neurotoxin is removed or modified. More preferably, the $H_C$ of the neurotoxin, such as *botulinum* toxin type A, is removed.

In another embodiment, the L chain of a clostridial neurotoxin, or a fragment of the L chain of a clostridial neurotoxin containing the endopeptidase activity, is covalently coupled to a targeting moiety. The covalent linkages used to couple the components of the agents may include appropriate spacer regions.

In a preferred embodiment, the agent comprises the $H_N$, the L chain and the targeting moiety, covalently linked together.

The targeting moiety preferably is derived from an amino acid. In one embodiment of the present invention, the targeting moiety is glutamate, since glutamate is recognized as a neurotransmitter that is released in the transmission of pain signals.

In another preferred embodiment, the amino acids from which the targeting moiety is derived link to form a peptide which is one of the peptides released for the transmission of pain signals. For example, such peptides include neuropeptide Y, calcitonin-gene related peptide (CGRP), substance P and the like, preferably substance P.

In another embodiment, the targeting moiety can be a transmission compound which is, or which is substantially similar to a neurotransmitter, which is released by a neuron to initiate or to propagate the transmission of, or which facilitates the generation of, a pain signal. Thus, as used herein the phrase "transmission compound" means a compound which is made by a neuron and which is secreted or released extracellularly (e.g. into a synaptic cleft or synaptic gap) by the neuron. Additionally, the transmission compound is a nociceptive compound, meaning that the transmission compound has a significant influence upon the generation and/or perception of pain (i.e. a "pain signal") in response to a nociceptive event. A nociceptive event can be, for example, an inflammation, trauma, or a neuropathic syndrome. A preferred group of transmission compounds can be selected from the tachykinin family of which substance P is a member. Examples of such tachykinins include physalaemin, kassinin, uperolein, eledoisin, and substance K. Additionally, substance P precursors, fragments, analogues comprising at least one D-amino acid and analogues comprising a disulfide bond may also be used as a targeting moiety.

In one embodiment of the present invention, the agent comprises a clostridial neurotoxin component (i.e. L-$H_N$) or parts thereof, covalently attached or coupled to substance P.

In a preferred embodiment of the present invention, the agent comprises a *botulinum* neurotoxin toxin type A, or parts thereof, covalently coupled to substance P. In an additional preferred embodiment of the present invention, the agent comprises *botulinum* toxin neurotoxin type A, wherein the $H_C$ of the *botulinum* neurotoxin type A is modified, more preferably removed or deleted, and the remaining toxin (i.e. with the $H_C$ removed) is then covalently coupled to substance P.

In another embodiment of this invention, the agent comprises an L chain of a clostridial neurotoxin, or a fragment of the L chain containing the endopeptidase activity, coupled to substance P. Preferably, the L chain or fragment of the L chain is derived from *botulinum* toxin type A.

The agents disclosed herein comprise a polypeptide, with a first and second amino acid sequence regions. The first region preferably includes a first domain and a second domain. Preferably, the first domain comprises a targeting moiety, and the second domain comprises an $H_N$. The targeting moiety is the same as described above. The $H_N$ preferably is derived from Clostridial *botulinum* type A and is able to facilitate the transfer of the entire polypeptide, or portions of the polypeptide, preferably the second amino acid region, across an intracellular endosome membrane into the cytosol of the neuron.

The second amino acid sequence region preferably comprises the L chain. Without wishing to limit the invention to any particular theory or mechanism of operation, it is believed that the L chain is an effective therapeutic element having biological activity because, as discussed above, once it is translocated inside the neuron it interferes with the exocytosis process of a neurotransmitter.

In another broad aspect of this invention, the present agents are expressed recombinantly with the targeting moiety, as a fusion protein therefore.

In one embodiment, recombinant techniques are used to produce the clostridial neurotoxin components of the present agents. The technique includes generating genetic constructs which have codes for clostridial neurotoxins, modified clostridial neurotoxins, or fragments thereof. The genetic constructs are then fused with cloning vectors, such as plasmids, and are incorporated into a host cell for amplification. The expressed clostridial components can then be then isolated by conventional and known techniques.

A clostridial neurotoxin expressed recombinantly without a targeting moiety can be chemically coupled to a targeting moiety (conjugate formation). Preferably, the linkages between the clostridial components and the targeting moieties include appropriate spacer regions.

In another embodiment, the genetic constructs include genes coding for both the clostridial neurotoxin components and the targeting moieties. Additionally, the genetic constructs may include genes coding for appropriate spacer regions between the clostridial neurotoxin components and the targeting moieties.

In another broad aspect of this invention, there are provided methods for treatment of pain which comprise administering effective doses of the agents according to the invention. The routes of administration preferably include administration locally to the spine and locally to the peripheral location of pain.

In one embodiment, the present agents in therapeutically effective amounts, for example, between about 1 U and about 500 U, can be administered, for example, intraspinally administered, to alleviate pain experienced by a mammal. Preferably the amounts are between about 10 U and about 300 U. More preferably the amount is between about 20 and 250 units, such about 50 U to 200 U or 70 U.

In a human patient, the therapeutically effective doses (for agents derived from *botulinum* toxin type A) are in the amounts between about $10^{-3}$ U/kg and about 35 U/kg. Preferably, the agents used are administered in amounts between about 1 U/kg and about 10 U/kg. More preferably, the agents are administered in amounts of about 3 U/kg. Significantly, the pain alleviating effect of the present agents can persist for between about 2–6 months per administration.

The intraspinal administrations of the agents are preferably by intrathecal administration, such as intrathecally to a cranial, cervical, thoracic, lumbar, sacral or coccygeal region of the central nervous system and the administration step can include the steps of accessing a subarachnoid space of the central nervous system of the mammal, and injecting the agents into the subarachnoid space. The accessing step can be carried out by affecting a spinal tap.

Alternately, the intraspinal administration step can include the steps of catheterization of a subarachnoid space of the central nervous system of the mammal, followed by injection of the agents through a catheter inserted by the catheterization step into the subarachnoid space. Note that prior to the injecting step there can be the step of attaching to or implanting in the mammal an administration means for administering the agents to the central nervous system of the mammal. The administration means can be made up of a reservoir of the agents, where the reservoir is operably connected to a pump means for pumping an aliquot of the agents out of the reservoir and into an end of the catheter in the subarachnoid space.

Each and every feature described herein, and each and every combination of two or more of such features, is included within the scope of the present invention provided that the features included in such a combination are not mutually inconsistent.

Definitions

Light chain means the light chain of a clostridial neurotoxin. It has a molecular weight of about 50 kDa, and can be referred to as L chain, L or as the proteolytic domain (amino acid sequence) of a clostridial neurotoxin.

Heavy chain means the heavy chain of a clostridial neurotoxin. It has a molecular weight of about 100 kDa and can be referred to as H chain or as H.

$H_c$ means a fragment (about 50 kDa) derived from the H chain of a clostridial neurotoxin which is approximately equivalent to the carboxyl end segment of the H chain, or the portion corresponding to that fragment in the intact H chain. It is believed to be immunogenic and to contain the portion of the natural or wild type clostridial neurotoxin involved in high affinity, presynaptic binding to motor neurons.

$H_N$ means a fragment (about 50 kDa) derived from the H chain of a clostridial neurotoxin which is approximately equivalent to the amino end segment of the H chain, or the portion corresponding to that fragment in the intact H chain. It is believed to contain the portion of the natural or wild type clostridial neurotoxin involved in the translocation of the L chain across an intracellular endosomal membrane.

$LH_N$ or $L\text{-}H_N$ means a fragment derived from a clostridial neurotoxin that contains the L chain, or a functional fragment thereof coupled to the $H_N$ domain. It can be obtained from the intact clostridial neurotoxin by proteolysis, so as to remove or to modify the $H_C$ domain.

Targeting moiety means a molecule that has a specific binding affinity for a cell surface receptor, for example, for a neuronal receptor so as to influence the transmission or reception of pain signals by the neuron.

Importantly, the agents disclosed herein are preferably administered by local administration, that is directly to the site where a therapeutic effect is desired.

DESCRIPTION

This invention is based upon the discovery that pain can be treated by administration to a patient of an agent which is comprised of a derivative of a clostridial neurotoxin and a targeting moiety, where the targeting moiety is selected from the group consisting of transmission compounds which can be released from a neuron upon the initiation, transmission of, or facilitation of the generation of, a pain signal by the neuron.

Significantly, the agents of the present invention can alleviate pain without being cytotoxic to their target neurons. Furthermore, agents within the scope of the present invention can be administered to both central nociceptive neurons and to primary sensory afferent neurons.

The mechanism of action for these agents in alleviating pain is currently not fully understood. Without wishing to limit the invention to any particular theory or mechanism of operation, it is believed that, at least with respect to areas in spinal cord, the agents disclosed herein target neurons having receptors for neurotransmitters that are released by neurons for or upon the transmission of pain signals. For example, when the targeting moiety is substance P, the agent is thought to interact with neurons expressing substance P receptors (SPR), such as projection neurons. Moreover, the receptors binding neurotransmitters released for the transmission of pain are primarily expressed on cells involved in the transmission of pain signals. For example, with respect to the central nervous system, it is well known that substance P receptors are primarily expressed on projection neurons in the dorsal horn of the spinal cord. See e.g. Vigna et al, *J. Neuroscience*, 14(2):834–845 (1994).

Therefore, the agents as described in this invention preferably are very specific for treating pain because they do not substantially or significantly interact and/or interfere with neurons and cells of other systems. Moreover, it is believed that the agents of this invention may enter into these specific neurons, for example projection neurons, through an endocytosis process. Once inside the neurons, it is further believed that the $H_N$ of these agents facilitate the translocation of the agent into the cytosol. In the cytosol, the agent, or a component thereof, can inhibit the release of a neurotransmitter involved in the further transmission of pain signals. It is further believed that the L chain of the clostridial neurotoxin component of the agent is responsible for the inhibition of the release of neurotransmitters that are involved in pain transmission by interfering with their vesicular exocytosis.

Additionally, the agents of this invention also provide pain alleviating effects when locally applied to peripheral pain sites. Also without wishing to limit the invention to any particular theory or mechanism of operation, it is believed that the agents interfere with the functions of cells having receptors for nociception, for example orphanin, substance P and/or kyotorphin, at the peripheral locations. See Ueda, *Jpn J. Pharmacology*, 79(3):263–268, the content of which is incorporated in its entirety herein by reference. These cells are uniquely involved in pain transmissions and the disruption of their functions by the agents can result in pain alleviation. Furthermore, it is believed that the mechanism for the inhibitory effects by agents in these cells is similar to that described above. Moreover, these agents can also bind, enter into and interfere with the function of primary sensory neurons.

According to one broad aspect of the invention, the clostridial neurotoxin component is covalently coupled to a targeting moiety. The clostridial neurotoxin component is a polypeptide and may be derived from Clostridial *beratti*, Clostridial *butyricum*, or Clostridial *botulinum*. More preferably, the *clostridium* neurotoxin component is derived from Clostridial *botulinum*. Clostridial *botulinum* produces *botulinum* toxin types A, B, C, D, E, F and G. Although any of these toxin types may be used in the present invention, *botulinum* type A is more preferably used.

Furthermore, the clostridial neurotoxin component may comprise only a fragment of the entire neurotoxin. For example, it is known in the art that the $H_c$ of the neurotoxin molecule can be removed from the other segment of the H chain, the $H_N$, such that the $H_N$ fragment remains disulphide linked to the L chain of the neurotoxin molecule to provide a fragment known as the $LH_N$. Thus, in one embodiment of the present invention the $LH_N$ fragment of a clostridial neurotoxin is covalently coupled, using linkages which may include one or more spacer regions, to a targeting moiety.

In another embodiment of the invention, the domain having the $H_c$ of a clostridial neurotoxin is removed, mutated or modified, e.g. by chemical modification, to reduce, or preferably incapacitate, its ability to bind the neurotoxin to receptors at the neuromuscular junction. This modified clostridial neurotoxin is then covalently coupled, using linkages which may include one or more spacer regions, to a targeting moiety.

In another embodiment of the invention, the H chain of a clostridial neurotoxin, in which the $H_c$ is removed, mutated or modified, e.g. by chemical modification, to reduce, preferably incapacitate, its ability to bind the neurotoxin to receptors at the neuromuscular junction is combined with the L-chain of a different clostridial neurotoxin, to form a hybrid. For example, in one embodiment, the clostridial neurotoxin component comprises an H chain with the $H_c$ removed, mutated or modified derived from *botulinum* toxin type A, and an L chain derived from another *botulinum* toxin type. The described hybrid is covalently coupled to a targeting moiety, preferably with one or more spacer regions.

In another embodiment of the invention, the L chain of a clostridial neurotoxin, or a fragment of the L chain containing the endopeptidase activity, is linked, using linkages which may include one or more spacer regions, to a targeting moiety which can also effect the internalization of the L chain, or fragment thereof containing endopeptidase activity, into the cytoplasm of the cell.

In a preferred embodiment, the agent comprises the $H_N$ the L chain and the targeting moiety, covalently linked together. The targeting moiety according to the first aspect of the invention is preferably derived from amino acids, substituted counterparts thereof and mixtures thereof. The term "substituted counterparts thereof" as it relates to any of the above noted amino acids refers to molecules that are functionally and physically similar to the amino acids, either as independent units or units incorporated into macromolecules, for example, peptides.

In one preferred aspect of the present invention, the targeting moiety is glutamate, since glutamate is the predominant neurotransmitter at the synapses between primary afferents and projection neurons. In another embodiment, the targeting moieties may be components that are substantially similar to the transmission compounds, for example, glutamate, in this particular instance. Hereinafter, the term "components that are substantially similar to the transmission compounds," is defined as molecules or substances that have the same functions as that of the transmission compounds, for example, binding to receptors that are involved in the transmission of pain signals.

In one embodiment, components that are substantially similar to glutamate are agonists of glutamate. For example, components substantially similar to glutamate are quisqualate, DL-alpha-amino-3-hydroxy-5-methylisoxazole-4-propionate, N-Me-D-aspartate, kinate and the like. Additionally, components substantially similar to glutamate may also include antagonists of glutamate. For example, these molecules include 6-cyano-7nitroquinozaline-2,3-dione, 3-(2-carboxypiperazin-4-yl)propyl-1-phosponic acid, lactonized kainate and the like.

In a more preferred embodiment, the amino acids link to form one of the peptides which are released by neurons for the transmission of pain signals. For example, these peptides include neuropeptide Y and calcitonin-gene related peptide (CGRP). Even more preferably, the peptide is substance P.

In another embodiment, components substantially similar to substance P may be used as targeting moieties. These components include substance P precursors, fragments, analogs and/or derivatives. The history, isolation, identification, and synthesis of substance P and its precursors, fragments, analogs and/or derivatives are disclosed in U.S. Pat. No. 5,891,842 (incorporated herein by reference in its entirety)

Substance P is an 11 amino acid peptide which has a number of different natural and synthetic precursor forms; has been demonstrated to be converted into a variety of naturally occurring amino-terminal peptide fragments; and can be obtained in analog format compromising, substituted counterparts thereof, for example, lysine methyl ester, D-amino acids or disulfide bridges substitutions, thereby yielding more stable and discriminating formulations. A representative listing of substance P and its related chemical entities is provided by Table 1 below. The amino acid sequence (1) in Table 1 (Arg-Pro-Lys-Pro-Gln-Gln-Phe-Phe-Gly-Leu-Met-amide) can be referred to a SEQ ID NO:1, and the subsequent 17 amino acid sequences set forth in Table one can be similarly identified as SEQ ID NO:2 to SEQ ID NO:18.

TABLE 1

Substance P, And Representative Precursors,
Fragments, And Stabilized Or Substituted Analogs

| Name | Formula |
|---|---|
| (1) Substance P | Arg-Pro-Lys-Pro-Gln-Gln-Phe-Phe-Gly-Leu-Met-amide (SEQ ID NO:1) |
| Natural Precursors: | |
| (2) Substance P-Glycine* | Arg-Pro-Lys-Pro-Gln-Gln-Phe-Phe-Gly-Leu-Met-Gly (SEQ ID NO:2) |
| (3) Substance P-Glycine-Lysine* | Arg-Pro-Lys-Pro-Gln-Gln-Phe-Phe-Gly-Leu-Met-Gly-Lys (SEQ ID NO:3) |
| (4) Substance P-Glycine-Lysine-Arginine* | Arg-Pro-Lys-Pro-Gln-Gln-Phe-Phe-Gly-Leu-Met-Gly-Lys-Arg (SEQ ID NO:4) |
| Carboxy-Ester Synthetic Precursors: | |
| (5) Substance P-Glycine Methyl Ester° | Arg-Pro-Lys-Pro-Gln-Gln-Phe-Phe-Gly-Leu-Met-Gly-OMe (SEQ ID NO:5) |
| (6) Substance P-Glycine-Lysine-Methyl Ester° | Arg-Pro-Lys-Pro-Gln-Gln-Phe-Phe-Gly-Leu-Met-Gly-Lys-OMe (SEQ ID NO:6) |
| (7) Substance P-Glycine-Lysine Arginine Methyl Ester° | Arg-Pro-Lys-Pro-Gln-Gln-Phe-Phe-Gly-Leu-Met-Gly-Lys-Arg-OMe (SEQ ID NO:7) |
| (8) Substance P-Glycine-Ethyl Ester° | Arg-Pro-Lys-Pro-Gln-Gln-Phe-Phe-Gly-Leu-Met-Gly-OEth (SEQ ID NO:8) |
| (9) Substance P-Glycine-Lysine Ethyl Ester° | Arg-Pro-Lys-Pro-Gln-Gln-Phe-Phe-Gly-Leu-Met-Gly-Lys-OEth (SEQ ID NO:9) |
| (10) Substance P-Glycine-Lysine-Arginine Ethyl Ester° | Arg-Pro-Lys-Pro-Gln-Gln-Phe-Phe-Gly-Leu-Met-Gly-Lys-Arg-OEth (SEQ ID NO:10) |
| Naturally-Occurring Amino-Terminal Peptide Fragments: | |
| (11) Substance P/1–4# | Arg-Pro-Lys-Pro (SEQ ID NO:11) |
| (12) Substance P/1–7# | Arg-Pro-Lys-Pro-Gln-Gln-Phe (SEQ ID NO:12) |
| (13) Substance P/1–9# | Arg-Pro-Lys-Pro-Gln-Gln-Phe-Phe-Gly (SEQ ID NO:13) |
| Analogs Comprising Synthetic D-Amino Acids Or Disulfide (Cys-Cys) Bridges: | |
| (14) [D-Pro2, D-Phe7, D-Trp9]-Substance P′ | Arg-D-Pro-Lys-Pro-Gln-Gln-D-Phe-Phe-D-Trp-Leu-Met-amide (SEQ ID NO:14) |
| (15) [D-Pro2, D-Phe7, D-Trp9]-(Substance P-(Glycine′ | Arg-D-Pro-Lys-Pro-Gln-Gln-D-Phe-Phe-D-Trp-Leu-Met-Gly (SEQ ID NO:15) |
| (16) [D-Pro2, D-Trp7, D-Trp9]-Substance P′ | Arg-D-Pro-Lys-Pro-Gln-Gln-D-Trp-Phe-D-Trp-Leu-Met-amide (SEQ ID NO:16) |
| (17) [D-Pro2, D-Trp-7, D-Trp9]-Substance P-Glycine′ | Arg-D-Pro-Lys-Pro-Gln-Gln-D-Trp-Phe-D-Trp-Leu-Met-Gly (SEQ ID NO:17) |
| (18) [Cys3, Cys6, Tyr8, Pro10]-Substance P′ | Arg-Pro-Cys-Pro-Gln-Cys-Phe-Tyr-Gly-Pro-Met-amide (SEQ ID NO:18) |

*Shimonka et al., J. Neurochem. 59:81–92 (1992).
°Lee et al., Eur. J. Biochem. 114:315–327 (1981); Pernow, B., Pharmacol. Rev. 35:86–138 (1983); and Regoli et al., TIPS 9:290–295 (1988).
Stewart et al., Nature 262:784–785 (1986); and Skilling et al., J Neurosci. 10:1309–1318 (1990).
′Lavielle et al., Biochem. Pharmacol. 37:41 (1988); and Quirion, R. and T. V. Dam, Regulatory Peptides 22:18 (1988).

The components substantially similar to substance P may also include molecules in the same family as that of substance P. For example, a preferred family of such molecules would be the tachykinin family to which substance P is a member. Examples of some family members of tachykinins include physalaemin, kassinin, uperolein, eledoisin, substance K and the like.

In a preferred embodiment, the agent comprises a clostridial neurotoxin component, for example $LH_N$, coupled to substance P. In another preferred embodiment, the agent comprises a hybrid of two clostridial neurotoxins, such as the H chain, preferably $H_N$, derived from *botulinum* toxin A and the L chain derived from another *botulinum* toxin, coupled to substance P. In another preferred embodiment, the clostridial component of the agent is a *botulinum* toxin type A in which the $H_c$ has been removed or modified, coupled to substance P.

In another preferred embodiment, the agent comprises an L chain of a clostridial neurotoxin, or a fragment of the L chain containing the endopeptidase activity, coupled substance P. Even more preferably, the L chain or fragment of the L chain is derived from *botulinum* toxin A, and is coupled to substance P. Additionally, it is preferred that the L chain coupled to the substance P is covalently linked to $H_N$.

The clostridial components and the targeting moieties are coupled by covalent linkages. In a preferred embodiment, the linkages may include appropriate spacer regions. Spacer regions have many functions within this invention. For example, one of the functions of the spacer regions is to provide for adequate distance between the clostridial neurotoxin components and the targeting moieties so that the two components can independently and freely move about, without an internal steric hindrance.

In one embodiment, the spacer region is made up of sugar molecules, for example, saccharides, glucose, etc. In another embodiment, the spacer region may be constructed from an aliphatic chain. In another embodiment, the spacer regions may be constructed by linking together a series of amino acids, preferably glycine because they are small and are devoid of any functional group. In yet another embodiment, the spacer region may comprise one or more of the sugar molecules, aliphatic chains, and amino acids.

Also, these agents can be thought of as being polypeptides, with a first and a second amino acid sequence region. The first region preferably includes a first domain and a second domain. Preferably, the first domain of the first amino acid sequence comprises a targeting moiety. In one embodiment, the targeting moiety is able to bind to surface receptors of the spinal cord neurons under physiological conditions. More preferably, the targeting moiety specifically binds a receptor on a spinal cord dorsal horn neuron, for example a projection neuron.

Preferably, the second domain comprises a heavy chain or a portion thereof of a clostridial neurotoxin. Even more preferably, the $H_N$ of the heavy chain is able to facilitate the transfer of the polypeptide across an endosome membrane into the cytosol of the neuron. In one embodiment, the second domain of the first amino acid sequence comprises a clostridial neurotoxin heavy chain. More preferably, the clostridial neurotoxin heavy chain is derived from *Clostridium botulinum* neurotoxin type A. Even more preferably, the heavy chain is derived from the $H_N$ of *Clostridium botulinum* neurotoxin type A. In yet another embodiment, the heavy chain may be derived from Clostridial *botulinum* types B, C, D, E, F, G and mixtures thereof. Also, the heavy chain may be derived from Clostridial *baratii* and Clostridial *butyricum*. Additionally, the heavy chain, preferably the $H_N$, may be derived from Clostridial *tetani*.

The second amino acid sequence region preferably comprises the L chain. The L chain is the effective therapeutic element having biological activity because, as discussed above, once it is transferred inside the neuron it interferes with the exocytosis process of neurotransmitter. Preferably, the light chain is derived from Clostridial *botulinum* neurotoxin type A. According to another broad aspect of this invention recombinant techniques are used to produce the clostridial neurotoxin components of the agents. The technique includes steps of obtaining genetic materials from either DNA cloned from natural sources, or synthetic oligonucleotide sequences, which have codes for clostridial neurotoxin components including clostridial neurotoxins, modified clostridial neurotoxins and fragments thereof. The genetic constructs are incorporated into host cells for amplification by first fusing the genetic constructs with a cloning vectors, such as phages or plasmids. Then the cloning vectors are inserted into hosts, preferably *E. coli*'s. Following the expressions of the recombinant genes in host cells, the resultant proteins can be isolated using conventional techniques. The clostridial neurotoxin components derived from the recombinant techniques can then be chemically coupled to targeting moieties. Preferably, the linkages between the clostridial components and the targeting moieties include appropriate spacer regions.

In another embodiment, the genetic constructs include genes coding for both the clostridial neurotoxin components and the targeting moieties, for example, forming fusion proteins. Additionally, the genetic constructs may include genes coding for appropriate spacer regions between the clostridial neurotoxin components and the targeting moieties. From this aspect, the agents may be thought of as polypeptides comprising a first amino acid sequence region and a second amino acid sequence region. The first region may further comprise a first domain and a second domain. The details of these regions and domains are described above.

In another embodiment, the required $L$-$H_N$, which may be a hybrid of an L chain and an $H_N$ from different clostridial toxin types, is expressed recombinantly as a fusion protein. Such $LH_N$ hybrid may also be coupled to the targeting moiety, which may further include one or more spacer regions between them.

In another embodiment of the invention the L chain of a clostridial neurotoxin, or a fragment of the L chain containing the endopeptidase activity, is expressed recombinantly as a fusion protein with the $H_N$ of the H chain and the targeting moiety which can also affect the internalization of the L chain, or fragment thereof containing the endopeptidase activity, into the cytoplasm of the cell. The expressed fusion protein may also include one or more spacer regions.

There are many advantages to producing these agents recombinantly. For example, production of neurotoxin from anaerobic *Clostridium* cultures is a cumbersome and time-consuming process including a multi-step purification protocol involving several protein precipitation steps and either prolonged and repeated crystallization of the toxin or several stages of column chromatography. Significantly, the high toxicity of the product dictates that the procedure must be performed under strict containment (BL-3). During the fermentation process, the folded single-chain neurotoxins are activated by endogenous clostridial proteases through a process termed nicking. This involves the removal of approximately 10 amino acid residues from the single-chain to create the dichain form in which the two chains remain covalently linked through the intrachain disulfide bond.

The nicked neurotoxin is much more active than the unnicked form. The amount and precise location of nicking varies with the serotypes of the bacteria producing the toxin. The differences in single-chain neurotoxin activation and, hence, the yield of nicked toxin, are due to variations in the type and amounts of proteolytic activity produced by a given strain. For example, greater than 99% of Clostridial *botulinum* type A single-chain neurotoxin is activated by the Hall A Clostridial *botulinum* strain, whereas type B and E strains produce toxins with lower amounts of activation (0 to 75% depending upon the fermentation time). Thus, the high toxicity of the mature neurotoxin plays a major part in the commercial manufacture of neurotoxins as therapeutic agents.

The degree of activation of engineered clostridial toxins is, therefore, an important consideration for manufacture of these materials. It would be a major advantage if neurotoxins such as *botulinum* toxin and tetanus toxin could be expressed, recombinantly, in high yield in rapidly-growing bacteria (such as heterologous *E. coli* cells) as relatively non-toxic single-chains (or single chains having reduced toxic activity) which are safe, easy to isolate and simple to convert to the fully-active form.

With safety being a prime concern, previous work has concentrated on the expression in *E. coli* and purification of individual H and L chains of tetanus and *botulinum* toxins; these isolated chains are, by themselves, non-toxic; see Li et al., *Biochemistry* 33:7014–7020 (1994); Zhou et al., *Biochemistry* 34:15175–15181 (1995), hereby incorporated by reference herein. Following the separate production of these peptide chains and under strictly controlled conditions the H and L subunits can be combined by oxidative disulphide linkage to form the neuroparalytic di-chains.

In another broad aspect of this invention, methods are provided for the treatment of pain which comprise administering effective doses of the agents according to the invention. The agents described in this invention can be used in vivo, either directly formulated or as a pharmaceutically acceptable salt, for treatment of pain.

For example, in a preferable embodiment, agents according to the invention can be administered by spinal injection (epidural or intrathecal) at the level of the spinal segment involved in the innervation of an affected organ for the treatment of pain. This is, for example, applicable in the treatment of deep tissue pain, such as chronic malignant pain.

As used herein "intraspinal" means into or within the epidural space, the intrathecal space, the white or gray matter of the spinal cord or affiliated structures such as the dorsal root and dorsal root ganglia.

Preferably, clostridial neurotoxin components of agents used to practice a method within the scope of the present invention comprise *botulinum* toxins, such as one of the type A, B, C, D, E, F or G. Preferably, the *botulinum* toxin used is *botulinum* toxin type A, because of its high potency in humans and ready availability. The targeting moiety of the agents used to practice the method herein is preferably a substance P.

An intraspinal route for administration of a neurotoxin according to the present disclosed invention can be selected based upon criteria such as the solubility characteristics of the agents chosen as well as the amount of the agents to be administered. The amount of the agents administered can vary widely according to the particular disorder being treated, its severity and other various patient variables including size, weight, age, and responsiveness to therapy. For example, the extent of the area of CNS afferent pain neuron somata influenced is believed to be proportional to the volume of agents injected, while the quantity of the analgesia is, for most dose ranges, believed to be proportional to the concentration of agents injected. Furthermore, the particular intraspinal location for agents administration can depend upon the dermosome location of the pain to be treated. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill).

Preferably, the intraspinal administration is carried out intrathecally because of the greater ease in which the relatively larger intrathecal space is accessed and because the preferred agents generally exhibits low solubility in the lipid rich epidural environment. It is found that both inflammatory and neuropathic pain can be effectively treated by the disclosed methods without significant muscle spasticity or flaccidity or other side effects.

Intraspinal administration of the agents according to the present invention can be by various routes such as by catheterization or by spinal tap injection. The long lasting nature of the therapeutic effects of the present invention substantially removes the need for chronic antinociceptive drug administration, so that the present methods are advantageously practiced by infrequent spinal tap injection of the agents. Additionally, an intrathecal spinal tap agents administration route facilitates a more precise and localized delivery of agents with less danger of damage to the CNS, as compared to moving a catheter to access other CNS locations.

Intrathecal agents can be administered by bolus injection or by catheterization. The catheter can be inserted at L3-4 or at L4-5, a safe distance from the spinal cord which in humans terminates at L1, and guided upward in the subarachnoid space to rest at the desired site. For pain management, placement of the catheter or location of bolus injection by syringe depends on the site of the perceived pain, and the physicians preference. It is important to note that therapeutic agent administration according to the present disclosed methods can be carried out before the occurrence of or during the experience of a nociceptive event or syndrome.

It is found that an agent, such as the $LH_N$ (derived from *botulinum* toxin type A)-substance P, can be intraspinally administered according to the present disclosed methods in amounts between about 1 U to about 500 U. Preferably the amounts are between about 10 U and about 300 U. More preferably the amount is between about 10 and about 200 U, such as about 70 U.

In a human patient, the therapeutically effective doses (when the clostridial neurotoxin component is derived from a *botulinum* toxin type A) can be amounts between about $10^{-3}$ U/kg and about 35 U/kg. A dose of about $10^{-3}$ U/kg can result in an antinociceptive effect if delivered directly to or onto the dorsal horn of the CNS and/or if agents delivery is assisted by methods such as iontophoresis. Intraspinal administration of less than about $10^{-3}$ U/kg does not result in a significant or lasting therapeutic result. An intraspinal dose of more than 35 U/kg approaches a lethal dose of an agent such as the $L-H_N$ (derived from *botulinum* toxin type A)-substance P. It is desired that the agents used to obtain either antinociceptive effect contact the nerves of the CNS so as to favorably influence or down regulate the perception of pain in the innervated organ or tissue. Thus, intraspinal administration of agents by, for example, epidural injection can require an increase of the dosage by a factor of about ten to account for dilution of the agents upon diffusion from the epidural space to the intrathecal space and thence to the exterior nerves of the CNS.

A preferred range for intrathecal administration of an agent, such as the $LH_N$(type A)-substance P, so as to achieve an antinociceptive effect in the patient treated is from about $10^{-2}$ U/kg to about 10 U/kg. A more preferred range for intrathecal administration of an agent, such as the $LH_N$ (derived from *botulinum* toxin type A)-substance P, so as to achieve an antinociceptive effect in the patient treated is from about $10^{-1}$ U/kg to about 10 U/kg. Less than about $10^{-1}$ U/kg can result in the desired therapeutic effect being of less than the optimal or longest possible duration, while more than about 10 U/kg can still result in some symptoms of muscle flaccidity. A most preferred range for intrathecal administration of an agent, such as the $L-H_N$(derived from *botulinum* toxin type A)-substance P, so as to achieve an antinociceptive effect in the patient treated is from about 1 U/kg to about 10 U/kg. Intrathecal administration of an agent, such as the $L-H_N$(derived from *botulinum* toxin type A)-substance P, in this preferred range can provide dramatic therapeutic success. Furthermore, our experimental work indicates that a dose of about 3 U/kg can provide significant and long lasting antinociceptive effect without significant side effects for the treatment of inflammatory and neuropathic pain in human patients.

Although intraspinal administration of the agents is preferred for the treatment of pain, other routes of administration are possible. For example, the agent according to the invention can also be locally applied to a peripheral site of pain to alleviate such pain. A specific example of this is treatment by local application of the agents into a joint affected by inflammatory pain. Another example is treatment of muscular pain by subcutaneous, preferably intramuscular, injection of the agents into the location of pain.

The present invention includes within its scope the use of any agent which has a long duration antinociceptive effect when applied centrally or peripherally into a patient. For example, agents having the clostridial neurotoxin components made by any of the species of the toxin producing *Clostridium* bacteria, such as *Clostridium botulinum, Clostridium butyricum, Clostridium beratti* and *Clostridium tetani* can be used or adapted for use in the methods of the present invention. Additionally, all of the *botulinum* serotypes A, B, C, D, E, F and G can be advantageously used in the practice of the present invention, although type A is the most preferred and type B the least preferred, as explained above. Practice of the present invention can provide an analgesic effect, per injection, for 2 months or longer, for example 6 months, in humans.

EXAMPLES

The following examples provide those of ordinary skill in the art with specific preferred methods to produce the agents, example 1, and to treat pain, examples 2 through 8, within the scope of the present invention and are not intended to limit the scope of the invention.

Example 1

Recombinant Production of Agents

The production of a fusion of L-$H_N$ whereof the L chain is derived from *botulinum* toxin type B and the amine end segment of the H chain fragment is derived from *botulinum* toxin type A. The $H_N$ fragment of the *botulinum* toxin type A is produced according to the method described by Shone C. C., Hambleton, P., and Melling, J. (1987, Eur. J. Biochem. 167, 175–180) and the L chain of *botulinum* toxin type B according to the method of Sathyamoorthy, V. and Das-Gupta, B. R. (1985, J. Biol. Chem. 260, 10461–10466). The free cysteine on the amine end segment of the H chain fragment of *botulinum* toxin type A is then derivatized by the addition of a ten-fold molar excess of dipyridyl disulphide followed by incubation at 4 degree C. overnight. The excess dipyridyl disulphide and the thiopyridone by product are then removed by desalting the protein over a PD10 column (Pharmacia) into PBS.

The derivatized $H_N$ is then concentrated to a protein concentration in excess of 1 mg/ml before being mixed with an equimolar portion of L chain from *botulinum* toxin type B (>1 mg/ml in PBS). After overnight incubation at room temperature the mixture is separated by size exclusion chromatography over Superose 6 (Pharmacia), and the fractions analyzed by SDS-PAGE. The chimeric $LH_N$ is then available for dramatization to produce a targeted conjugate.

The example described above is purely illustrative of the invention. In synthesizing the agents, the coupling of the targeting moieties to the clostridial components, for example the modified clostridial neurotoxins or fragments thereof, is achieved via chemical coupling using reagents and techniques known to those skilled in the art. Thus, although the examples given use exclusively the PDPH/EDAC and Traut's reagent chemistry any other coupling chemistry capable of covalently attaching the targeting moieties of the agents to clostridial neurotoxin components and known to those skilled in the art is covered by the scope of this application. Similarly it is evident to those skilled in the art that either the DNA coding for either the entire composition of the agents or fragments of the agents could be readily constructed and, when expressed in an appropriate organism, could be used to recombinantly produce the agents or fragments of the agents. Such genetic constructs of the agents of the invention obtained by techniques known to those skilled in the art are also covered in the scope of this invention.

Example 2

Treatment of Inflammatory Pain by Intrathecal Administration of an Agent

A patient, age 45, experiencing acute inflammatory pain is treated by intrathecal administration, for example by spinal tap to the lumbar region, with between about 0.1 U/kg and 30 U/kg, (preferably from 20 U to 500 U), of an agent comprising an L-$H_N$ (derived from *botulinum* toxin type A)-substance P, the particular agent dose and site of injection, as well as the frequency of agent administrations depend upon a variety of factors within the skill of the treating physician, as previously set forth. Within 1–7 days after agent administration the patient's pain is substantially alleviated. The duration of pain reduction is from about 2 to about 6 months.

The agent can be injected at different spinal levels to treat different dermosomes, that is to treat pain in various body parts. Additionally, a catheter can be percutaneously inserted into the intrathecal space via lumbar puncture at vertebral level L3-4 or L4-5 using a Tuohy needle. When CSF flow is discernible a silastic catheter is threaded cephalad using a C-arm for verification of catheter placement. The catheter can be advanced to different vertebral locations and/or used at different dose concentrations to treat different types of pain and/or spasm. Thus, the catheter can be placed within the intrathecal space at the dermasomal level of the pain or spasm experienced.

Example 3

Treatment of Neuropathic Pain by Intrathecal Administration of an Agent

A patient, age 36, experiencing pain of neuropathic origin is treated by intrathecal administration through spinal tap to the lumbar region of between about 0.1 U/kg and 30 U/kg, (preferably from 20 U to 500 U), of an agent comprising an L-$H_N$ (derived from *botulinum* toxin type A)-substance P. Within 1–7 days the pain symptoms are substantially alleviated. The duration of pain reduction is from about 2 to about 6 months.

Example 4

Treatment of Pain Subsequent to Spinal Cord Injury by Intrathecal Administration of an Agent A patient, age 39, experiencing pain subsequent to spinal cord injury is treated by intrathecal administration, for example by spinal tap or by catheterization, to the spinal cord, such as to the lumbar region of the spinal cord, with between about 01 U/kg and 20 U/kg, (preferably between 20 U to 500 U), of an agent comprising an L-$H_N$ (derived from *botulinum* toxin type A)-substance P, the particular dose and site of injection, as well as the frequency of administrations depend upon a variety of factors within the skill of the treating physician, as previously set forth. Within 1–7 days after administration of the agent the patient's pain is substantially alleviated. The duration of pain reduction is from about 2 to about 6 months.

Example 5

Treatment of Pain Subsequent to Limb Injury by Intrathecal Administration of an Agent A patient, age 51, experiencing pain subsequent to injury to his hand, arm, foot or leg is treated by intrathecal administration, for example by spinal tap or by catheterization, to the spinal cord, such as to the lumbar region of the spinal cord, with between about 01 U/kg and 20 U/kg, (preferably from 20 U to 500 U), of an agent comprising L-$H_N$ (derived from *botulinum* neurotoxin type A)-substance P, the particular dose and site of injection, as well as the frequency of administrations depend upon a variety of factors within the skill of the treating physician, as previously set forth. Within 1–7 days after administration the patient's pain is substantially alleviated. The duration of pain reduction is from about 2 to about 6 months.

Example 6

Treatment of Pain Associated with Cancer by Intrathecal Administration of an Agent A patient, age 63, suffering from pain associated with cancer is treated by intrathecal administration, for example by spinal tap or by catheterization, to the spinal cord, such as to the lumbar region of the spinal cord, with between about 1 U/kg and 20 U/kg (preferably about 20 U to 500 U), of an agent comprising an $LH_N$ (derived from *botulinum* neurotoxin type A)-substance P, the particular dose and site of injection, as well as the frequency of administrations depend upon a variety of factors within the skill of the treating physician, as previously set forth. Within 1–7 days after administration the patient's pain is substantially alleviated. The duration of pain reduction is from about 2 to about 6 months.

Example 7

Treatment of Pain Associated with Diabetes by Intrathecal Administration of an Agent A patient, age 47, suffering from pain associated with diabetes is treated by intrathecal administration, for example by spinal tap or by catheterization, to the spinal cord, such as to the lumbar region of the spinal cord, with between about 0.1 U/kg and 30 U/kg, or 1 to 500 U, of an agent comprising an $L-H_N$ (derived from a *botulinum* neurotoxin type A)-substance P, the particular dose and site of injection, as well as the frequency of administrations depend upon a variety of factors within the skill of the treating physician, as previously set forth. Within 1–7 days after administration the patient's pain is substantially alleviated. The duration of pain reduction is from about 2 to about 6 months.

Example 8

Treatment of Pain Subsequent to Limb Injury by Peripheral Administration of an Agent A patient, age 35, experiencing pain subsequent to injury to his hand, arm, foot or leg is treated by intramuscular injection with between about 1 U/kg and 20 U/kg (preferably from 20 U to 500 U), of an agent comprising $L-H_N$ (derived from a *botulinum* neurotoxin type A)-substance P. The particular dose and site of injection, as well as the frequency of administrations depend upon a variety of factors within the skill of the treating physician, as previously set forth. Within 1–7 days after administration the patient's pain is substantially alleviated. The duration of pain reduction is from about 2 to about 6 months.

Although the present invention has been described in detail with regard to certain preferred methods, other embodiments, versions, and modifications within the scope of the present invention are possible. For example, a wide variety of neurotoxins can be effectively used in the methods of the present invention in place of clostridial neurotoxins. Additionally, the present invention includes intraspinal administration methods wherein two or more agents, such as two or more agents comprising different clostridial toxin components and targeting moieties, are administered concurrently or consecutively. For example, an agent comprising a an $LH_N$(*botulinum* neurotoxin type A)-substance P can be administered intraspinally until a loss of clinical response or neutralizing antibodies develop, followed by administration of an agent comprising $L-H_N$(derived from a *botulinum* neurotoxin type E)-substance P. While this invention has been described with respect to various specific examples and embodiments, it is to be understood that the invention is not limited thereto and that it can be variously practiced with the scope of the following claims.

SEQUENCE LISTING

```
<160> NUMBER OF SEQ ID NOS: 18

<210> SEQ ID NO 1
<211> LENGTH: 11
<212> TYPE: PRT
<213> ORGANISM: Unknown
<220> FEATURE:
<223> OTHER INFORMATION: Description of Unknown Organism:  This is a
      substance P and is very well known in the art.
<221> NAME/KEY: MISC_FEATURE
<222> LOCATION: (11)..(11)
<223> OTHER INFORMATION: Xaa at position 11 is Methionine Amide

<400> SEQUENCE: 1

Arg Pro Lys Pro Gln Gln Phe Phe Gly Leu Xaa
1               5                   10

<210> SEQ ID NO 2
<211> LENGTH: 12
<212> TYPE: PRT
<213> ORGANISM: Unknown
<220> FEATURE:
<223> OTHER INFORMATION: Description of Unknown Organism:  Precursor to
      substance P, which is very well known in the art.

<400> SEQUENCE: 2
```

Arg Pro Lys Pro Gln Gln Phe Phe Gly Leu Met Gly
1               5                   10

<210> SEQ ID NO 3
<211> LENGTH: 13
<212> TYPE: PRT
<213> ORGANISM: Unknown
<220> FEATURE:
<223> OTHER INFORMATION: Description of Unknown Organism:  This is a
      precursor to substance P and is very well known in the art.

<400> SEQUENCE: 3

Arg Pro Lys Pro Gln Gln Phe Phe Gly Leu Met Gly Lys
1               5                   10

<210> SEQ ID NO 4
<211> LENGTH: 14
<212> TYPE: PRT
<213> ORGANISM: Unknown
<220> FEATURE:
<223> OTHER INFORMATION: Description of Unknown Organism:  This is a
      precursor to substance P and is very well known in the art.

<400> SEQUENCE: 4

Arg Pro Lys Pro Gln Gln Phe Phe Gly Leu Met Gly Lys Arg
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence:  This is a
      carboxy-ester synthetic precursor to substance P.
<221> NAME/KEY: MISC_FEATURE
<222> LOCATION: (12)..(12)
<223> OTHER INFORMATION: Xaa at position 12 is Glycine Methyl Ester

<400> SEQUENCE: 5

Arg Pro Lys Pro Gln Gln Phe Phe Gly Leu Met Xaa
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence:  This is a
      carboxy-ester synthetic precursor to substance P.
<221> NAME/KEY: MISC_FEATURE
<222> LOCATION: (13)..(13)
<223> OTHER INFORMATION: Xaa at position 13 is Lysine Methyl Ester

<400> SEQUENCE: 6

Arg Pro Lys Pro Gln Gln Phe Phe Gly Leu Met Gly Xaa
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence:  This is a
      carboxy-ester synthetic precursor to substance P.
<221> NAME/KEY: MISC_FEATURE
<222> LOCATION: (14)..(14)
<223> OTHER INFORMATION: Xaa at position 14 is Arginine Methyl Ester

<400> SEQUENCE: 7

Arg Pro Lys Pro Gln Gln Phe Phe Gly Leu Met Gly Lys Xaa
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence:  This is a
      carboxy-ester synthetic precursor to substance P.
<221> NAME/KEY: MISC_FEATURE
<222> LOCATION: (12)..(12)
<223> OTHER INFORMATION: Xaa at position 12 is Glycine Ethyl Ester

<400> SEQUENCE: 8

Arg Pro Lys Pro Gln Gln Phe Phe Gly Leu Met Xaa
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence:  This is a
      carboxy-ester synthetic precursor to substance P.
<221> NAME/KEY: MISC_FEATURE
<222> LOCATION: (13)..(13)
<223> OTHER INFORMATION: Xaa at position 13 is Lysine Ethyl Ester

<400> SEQUENCE: 9

Arg Pro Lys Pro Gln Gln Phe Phe Gly Leu Met Gly Xaa
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence:  This is a
      carboxy-ester synthetic precursor to substance P.
<221> NAME/KEY: MISC_FEATURE
<222> LOCATION: (14)..(14)
<223> OTHER INFORMATION: Xaa at position 14 is Arginine Ethyl Ester

<400> SEQUENCE: 10

Arg Pro Lys Pro Gln Gln Phe Phe Gly Leu Met Gly Lys Xaa
1               5                   10

<210> SEQ ID NO 11
<211> LENGTH: 4
<212> TYPE: PRT
<213> ORGANISM: Unknown
<220> FEATURE:
<223> OTHER INFORMATION: Description of Unknown Organism:  This is a
      naturally occuring amino thermal peptide fragment derived from
      substance P.

<400> SEQUENCE: 11

Arg Pro Lys Pro
1

<210> SEQ ID NO 12
<211> LENGTH: 7
<212> TYPE: PRT
<213> ORGANISM: Unknown
<220> FEATURE:
<223> OTHER INFORMATION: Description of Unknown Organism:  This is a
      naturally occuring amino acid thermal peptide fragment derived
      from substance P.

```
<400> SEQUENCE: 12

Arg Pro Lys Pro Gln Gln Phe
1               5

<210> SEQ ID NO 13
<211> LENGTH: 9
<212> TYPE: PRT
<213> ORGANISM: Unknown
<220> FEATURE:
<223> OTHER INFORMATION: Description of Unknown Organism:  This is a
      naturally occuring amino thermal peptide frament derived from
      substance P.

<400> SEQUENCE: 13

Arg Pro Lys Pro Gln Gln Phe Phe Gly
1               5

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence:  This is an
      analog of substance P.
<221> NAME/KEY: MISC_FEATURE
<222> LOCATION: (2)..(11)
<223> OTHER INFORMATION: Xaa at position 2 is D-form of Proline, Xaa at
      position 7 is D-form of Phenylalanine, Xaa at position 9 is D-form
      of Tryptophan, Xaa at position 11 Methionine Amide

<400> SEQUENCE: 14

Arg Xaa Lys Pro Gln Gln Xaa Phe Xaa Leu Xaa
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence:  This is an
      analog of substance P.
<221> NAME/KEY: MISC_FEATURE
<222> LOCATION: (2)..(9)
<223> OTHER INFORMATION: Xaa at positon 2 is D-form of Proline, Xaa at
      position 7 is D-form of Phenylalanine, Xaa at position 9 is D-form
      of Tryptophan

<400> SEQUENCE: 15

Arg Xaa Lys Pro Gln Gln Xaa Phe Xaa Leu Met Gly
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence:  This is an
      analog of substance P.
<221> NAME/KEY: MISC_FEATURE
<222> LOCATION: (2)..(11)
<223> OTHER INFORMATION: Xaa at position 2 is D-form of Proline, Xaa at
      position 7 is D-form of Tryptophan, Xaa at position 9 is D-form of
      Tryptophan, Xaa at position 11 is Methionine Amide

<400> SEQUENCE: 16

Arg Xaa Lys Pro Gln Gln Xaa Phe Xaa Leu Xaa
1               5                   10

<210> SEQ ID NO 17
```

-continued

```
<211> LENGTH: 12
<212> TYPE: PRT
<213> ORGANISM: Artificial Sequence
<220> FEATURE:
<223> OTHER INFORMATION: Description of Artificial Sequence:  This is an
      analog of substance P.
<221> NAME/KEY: MISC_FEATURE
<222> LOCATION: (2)..(9)
<223> OTHER INFORMATION: Xaa at position 2 is D-form of Proline, Xaa at
      position 7 is D-form of Tryptophan, Xaa at position 9 is D-form of
      Tryptophan

<400> SEQUENCE: 17

Arg Xaa Lys Pro Gln Gln Xaa Phe Xaa Leu Met Gly
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence:  This is an
      analog of substance P.
<221> NAME/KEY: MISC_FEATURE
<222> LOCATION: (11)..(11)
<223> OTHER INFORMATION: Xaa at position 11 is Methionine Amide

<400> SEQUENCE: 18

Arg Pro Cys Pro Gln Cys Phe Tyr Gly Pro Xaa
1               5                   10
```

I claim:

1. An agent for treating pain comprising a modified *botulinum* neurotoxin comprising a *botulinum* neurotoxin $H_N$, a *botulinum* neurotoxin L chain, and no functional $H_C$ domain, the modified *botulinum* neurotoxin being covalently coupled to substance P so that the modified *botulinum* neurotoxin no longer binds to *botulinum* neurotoxin receptors at a neuromuscular junction with the same affinity as the native *botulinum* neurotoxin.

2. The agent of claim 1, wherein the *botulinum* neurotoxin is a *botulinum* toxin selected from the group consisting of serotype A, serotype B, serotype $C_1$, serotype D, serotype E, serotype F and serotype G.

3. The agent of claim 1, wherein the *botulinum* neurotoxin is *botulinum* toxin serotype A.

4. The agent of claim 1, wherein the agent is a fusion protein.

5. The agent of claim 1, wherein the L chain is obtained from a *botulinum* toxin selected from the group consisting of *botulinum* toxin serotype A, serotype B, serotype $C_1$, serotype D, serotype E, serotype F and serotype G.

6. The agent of claim 1, wherein the $H_N$ is obtained from a *botulinum* toxin selected from the group consisting of *botulinum* toxin serotype A, serotype B, serotype $C_1$, serotype D, serotype E, serotype F and serotype G.

* * * * *